United States Patent [19]

Karita et al.

[11] Patent Number: 4,846,932
[45] Date of Patent: Jul. 11, 1989

[54] WATER SETTING PAPER

[75] Inventors: Takeshi Karita, Chiba; Yoshiro Saito; Shunichiro Kuromatsu, both of Tokyo, all of Japan

[73] Assignee: Kuromatsu Corporation Co., Ltd., Tokyo, Japan

[21] Appl. No.: 943,645

[22] Filed: Dec. 17, 1986

[51] Int. Cl.⁴ .............. D21H 1/02; B32B 29/06; B32B 27/04; C08L 3/06
[52] U.S. Cl. .............. 162/127; 162/125; 162/164.1; 162/168.1; 162/169; 162/164.5; 162/164.6; 428/537.5; 428/326; 428/913; 525/32; 525/54; 524/734
[58] Field of Search .............. 428/537.5, 326, 913; 525/54, 32; 524/734; 162/125, 127, 164.5, 164.1, 168.1, 169, 164.6

[56] References Cited

U.S. PATENT DOCUMENTS

| | | | |
|---|---|---|---|
| 3,935,099 | 1/1976 | Weaver et al. | 524/734 |
| 4,076,663 | 2/1978 | Masuda | 525/54.31 |
| 4,619,862 | 10/1986 | Sokolowski et al. | 428/326 |

FOREIGN PATENT DOCUMENTS

| | | | |
|---|---|---|---|
| 0062930 | 5/1980 | Japan | 428/537.5 |
| 0067047 | 4/1984 | Japan | 428/537.5 |
| 2119709A | 11/1983 | United Kingdom | 428/537.5 |

Primary Examiner—P. C. Ives
Attorney, Agent, or Firm—Frishauf, Holtz, Goodman & Woodward

[57] ABSTRACT

Water setting paper (high water-absorbency material) comprised of pulp fiber, water-soluble resin and high wate-absorbency resin is produced in sheet form for use in urine containers or portable toilets. Water setting paper or the high water-absorbency sheet thus formed absorbs and solidifies the urine, allowing the urine to be disposed of easily, rapidly and hygienically.

12 Claims, 1 Drawing Sheet

WATER SETTING PAPER

BACKGROUND OF THE INVENTION

1. Field of the Invention

This invention relates to a water setting (water solidifying) paper or a high water-absorbency material in sheet form containing high water-absorbency resin.

2. Description of the Prior Art

It is generally known that paper produced from paper-making materials containing carboxymethylcellulose (CMC-H) or corboxyethylcellulose (CEC-H), and the respective aluminum salt, barium salt, zinc salt, tin salt and manganese salt thereof (CMC-Al, CMC-Ba, CMC-Zn, CMC-Sn, CMC-Mn, CEC-Al, CEC-Ba, CEC-Zn, CEC-Sn, CEC-Mn) are water-soluble or have the property of becoming rapidly dispersed in water. Water-soluble paper is utilized as the paper for secret documents and for water-soluble labels. Methods for manufacturing paper that is water-soluble or which disperses rapidly in water are disclosed in, for example, Japanese Laid-open Patent No. 38-(1963) 25,159, Japanese Laid-open Patent No. 39-(1964) 152, Japanese Laid-open Patent No. 40-(1965) 968, Japanese Laid-open Patent No. 42-(1967) 2,925, Japanese Laid-open Patent No. 43-(1968) 1,214 and Japanese Laid-open Patent No. 48-(1973) 27,605.

Also, because high water-absorbency resins of the grafted-starch series, cellulose series and polyacrylic acid series have higher water-absorbency than conventional water-absorbing materials such as cotton, cloth, sponge and tissue paper, they are used in sanitary napkins, paper diapers, underpads and the like.

High water-absorbency resin is used by encapsulation or inclusion of the resin in non-woven fabrics or pulp products such as tissue paper and the like which are then disposed at an inner portion of the sanitary napkin, paper diaper and so forth, so that the water content of the voided urine and the like passing through the paper is absorbed and solidified at the inner portion, with even the surface moisture of the paper itself being absorbed, providing the products with a clean feeling in use.

Disposal following urination has been a problem in the case of conventional urine containers such as urine bottles and portable toilets, the drawback being that urine that has been collected in the container is spilled when the container is moved or shaken, soiling the surroundings. To eliminate this drawback, conventionally high water-absorbency resin has been placed inside the urine bottle or other such urine container to solidify the urine. Another method that has been advanced has involved encapsulating the said high water-absorbency resin inside a non-woven fabric or pulp product, and inserting the thus-prepared product into the urine container.

However, because with this method the high water-absorbency resin is enveloped in pulp, it becomes interlocked with the long pulp fibers and is not easily dissolved. And with respect also to disposal, because it does not readily dissolve in water, it is not possible to flush it down flush toilets. Therefore the only way the product could be dissolved after use was by means of formerly used methods such as incineration.

With the method involving the spreading of high water-absorbency resin as it is in the urine container, the spreadig took time, and as the resin was inserted in particulate form, it had the drawback of being inconvenient to store and handle. Then again, because particulate resin reacts with small amounts of liquid and sets starting at the surface, resin which lies thereunder and not exposed to the surface loses any chance of being involved in the reaction owing to the setting of the surface resin. As a result, urine in many cases remains in the urine container in a state of incomplete reaction (agglomerate state). In order to activate it, it is necessary to stir up the underlying resin to bring it to the surface; but as this is unhygienic, it is usually disposed of in its entirety.

SUMMARY OF THE INVENTION

It is an object of this invention to provide a high water-absorbency material in sheet form water setting (water-solidifying) paper which enables the urine in a urine bottle or suchlike urine container or portable toilet to be disposed of easily, rapidly and hygienically and can be applied widely in many other ways.

The water setting paper or the high water-absorbency material in sheet form according to this invention comprises pulp fiber, water-soluble resin and high water-absorbency resin. The compound ratio of the fiber and resin is not an issue, but in order to raise the water absorbency it is preferable that the pulp fibers be kept to a small (trace) amount and the water-soluble resin and high water-absorbency resin be mixed in in a large amount (about 80%).

Methods for forming the sheet include the above method of mixing pulp fiber, water-soluble resin and high water-absorbency resin and forming it into sheet, a method whereby water-soluble paper consisting of pulp-fiber and water-soluble resin is used to sandwich the high water-absorbency resin, and a method whereby high water-absorbency resin is bonded to water-soluble paper. There is also a method wherein sheet formed from the said mixture of pulp-fiber, water-soluble resin and high water-absorbency resin is used to sandwich the high water-absorbency resin. Compared with the method whereby water-soluble paper is used to sandwich high water-absorbency resin, this provides an improved water-absorbency ratio because two high water-absorbency water-soluble sheets are used. Also, with the method using conventional water-soluble paper to sandwich the high water-absorbency resin, the finished sheet is thick and stiff, in addition to which if the amount of high water-absorbency resin is increased to raise the water-absorbency ratio, there has been the problem that the sheet loses resiliency, but with water-soluble paper containing high water-absorbency resin resiliency is retained. However, the water setting (solidifying) paper (the high water-absorbency sheet) according to this invention may be formed using any method of manufacture, laminate state or structure, provided it is in sheet form.

As the high water-absorbency resin for use in this invention, in addition to natural resins such as starch there may be utilized various synthetic resins produced by the crosslinking of polyacrylic acid, polystyrene sulfonic acid, polyvinyl pyridine, maleic anhydride, carboxylmethylcellulose, polyethylene oxide, polyvinyl alcohol, or cellulose ether. The high water-absorbency resin for use in this invention is not however limited to the above ones, which are examples of existing high water-absorbency resins; in addition to the above, any other resin which has high water-absorbency may also be utilized.

Also, carboxymethylcellulose (CMC-H) or carboxyethylcellulose (CEC-H) are often utilized as the water-soluble resin, but the respective aluminum salt, barium salt, zinc salt, tin salt and manganese salt thereof (CMC-Al, CMC-Ba, CMC-Zn, CMC-Sn, CMC-Mn, CEC-Al, CEC-Ba, CEC-Zn, CEC-Sn, CEC-Mn) may also be utilized. The water-soluble resin for use in this invention is not however limited to the above ones, which are examples of existing water-soluble resins; in addition to the above, any other resin which is water-soluble may also utilized. Moreover, if required by an application, paper-making materials such kraft pulp for paper-making, sulfite-pulp, soluble pulp for synthetic fiber and other such vegetable fibers, polyamide, polyester and other such synthetic fibers, glass fiber, asbestos and other inorganic fibers may be mixed in as required up to a proportion which does not impede dispersion and dissolution in water.

High water-absorbency resins are generally of a grafted-starch system, cellulose system, or polyacrylic acid system. It is known that when water-soluble resin is crosslinked, as the density of the crosslinks increases the nature of the resin changes, from water-solubility to water-growth, and then to merely lyophilic. High water-absorbency resin is an application of water-growth resin obtained from low-density crosslinking. That is, high water-absorbency resin is made by low-density crosslinking of water-soluble resin such as CMC, PVA, polyacrylic acid soda, starch-acrylic acid graft polymer, starch-acrylilonitrile graft polymer hydrozylates, and possesses high water-absorbency and low water-retentivity. Whereas pulp and tissue paper can absorb up to 20 times their own weight of water, high water-absorbency resin can absorb at least 50 to 500 times its own weight of water. Pulp or sponge only forms a state whereby water is occluded in the internal spaces thereof, so the water is easily ejected by the application of external pressure. When high water-absorbency resin comes into contact with water it reacts chemically, swelling and gelling, so that once water has been absorbed and it has swollen and jelled, water-retentivity is high, as water does not leak out even when an external pressure is applied.

High water-absorbency resin possessing these characteristics is sandwiched in layer form between the said water-soluble resin such as CMC-H and pulp fiber, or the high water-absorbency resin is mixed in during the paper-making process, to produce the high water-absorbency sheet of this invention. However, sandwiching the resin between pulp fiber layers involves a problem with regard to sheet flexibility, so there is a limit to the amount of high water-absorbency resin that is to be thus sandwiched, and accordingly the water-absorbency limit is 20 times its own weight. Therefore, it is preferable that high water-absorbency resin be mixed in during the paper-making process, and, if moreover high water-absorbency resin is sandwiched between sheets produced with high water-absorbency resin mixed therein it becomes possible to attain the said water-absorbency ratio of some 50 to 500 times.

When water setting paper (high water-absorbency sheet) formed as described above comes into contact with water or some other aqueous solution, because it contains the said CMC-H or the like the water setting paper (high water-absorbency sheet) first dissolves in the water, and the high water-absorbency resin contained in the water setting paper (high water-absorbency sheet) or which has been sandwiched therein dissolves in the water, the reaction starts, and the water content starts to set, swelling and gelling.

Where there is water content the water setting (solidifying) paper (high water-absorbency sheet) dissolves, but dissolution stops when a state of saturation is reached, leaving the water setting paper (high water-absorbency sheet) with portions which have dissolved and portions which are still in sheet form. With the next influx of water the portions of the remaining part of the water setting (water solidifying) paper (high water-absorbency sheet) involved melt, and the high water-absorbency resin contained inside the water setting paper (high water-absorbency sheet) or which has been sandwiched therein starts reaching, swelling and gelling.

Therefore, because unlike the conventional chemical agent (powder) form of high water-absorbency resin it is in the form of a sheet, it eliminates the drawback of underlying particles resulting in the agent setting without the reaction having taken place fully, so that it is possible to maintain a state in which additional moisture can be absorbed at any time. This is the merit of the entirely different sheet form, compared with the conventional chemical agent.

BRIEF DESCRIPTION OF THE DRAWINGS

The present invention will now be described in detail with reference to the attached drawings, where.

DESCRIPTION OF THE PREFERRED EMBODIMENT

Figure 1:
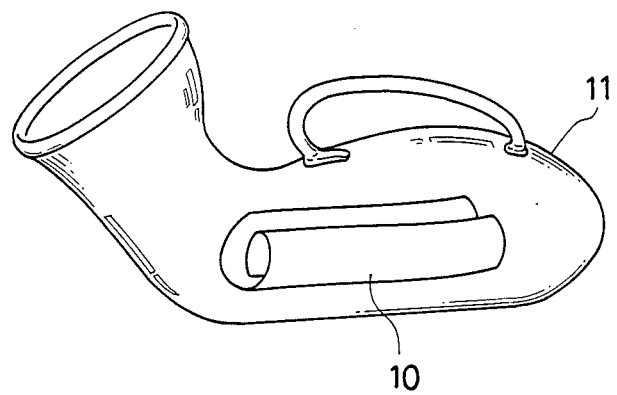
FIG. 1 is a perspective view showing the water setting paper (high under-absorbency sheet) of this invention, in place inside a urine container.
Figure 2:
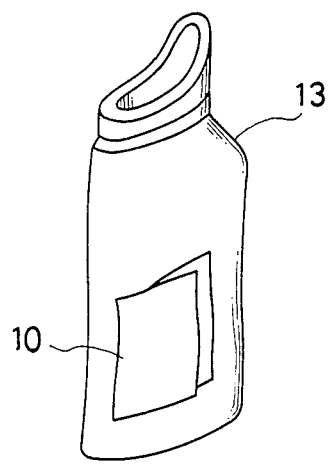
FIG. 2 is a perspective view of a portable toilet in which has been placed the water setting paper (highly water-absorbent sheet).

The water setting paper (high water-absorbency sheet) merely has to be placed in the urine container. In the case of the conventional high water-absorbency resin powder any tilting or shaking of the container could cause the agent to spill out, but with the water setting paper (high water-absorbency sheet) according to this invention there is no concern that such tilting or shaking may cause the inserted sheet to fall out.

When urine is voided into such a container, the paper component containing the said CMC-H or the like being water-soluble therefore disperses and dissolves in the urine, and as the water setting paper (high water-absorbency sheet) dissolves the high water-absorbency resin contained therein is exposed or is dissolved. Thus, the high water-absorbency agent starts to react, solidifying the water content, swelling and gelling. Moving or shaking the urine container does not therefore cause the urine therein to spill, so there is no soiling of the surroundings. Moreover, if high water-absorbency resin is placed inside the urine container as it is, irrespective of the amount of urine all of the resin is wetted, making further use thereof impossible, so that each time urination is performed all the resin must be replaced. However, when the high water-absorbency resin is formed integrally with paper, as in this invention, or when the intergrally manufactured sheet is utilized to sandwich high water-absorbency resin, it still has water-retention capability, which is to say it retains the sheet form, so re-use is possible and it is economical. Also, with respect to disposal, the gelled high water-absorbency resin can be easily washed out with water.

Furthermore, with the high water-absorbency resin reacting with the water content, solidifying it, the voided urine or the like does not come into contact with the air, so there is no release of unpleasant odors from the urine.

Thus, with the water setting (solidifying) paper (high water-absorbency sheet) according to the present invention and formed as described in the foregoing, by using high water setting paper (water-absorbency sheet) inserted in a urine container such as a urine bottle or a portable toilet, spillage of voided urine caused by moving or shaking the container can be prevented. Also, as the solidified urine can be flushed down the toilet, disposal of the urine is simple, quick and hygienic. In addition, the ease with which it can be handled and its water absorbency and water retentivity enable it to be applied widely, such as to sanitary napkins and paper diapers and the like.

We claim:

1. A water setting paper formed of high water-absorbency material in sheet form and comprising pulp fiber, water-soluble resin and high water-absorbency cross-linked resin formed into a sheet.

2. The water setting paper of claim 1 wherein the high water-absorbency resin is comprised of a synthetic resin produced by the crosslinking of polyacrylic acid, polystyrene sulfonic acid, polyvinyl pyridine, maleic anhydride, carboxylmethylcellulose, polyethylene oxide, polyvinyl alcohol or cellulose ether.

3. The water setting paper of claim 1 wherein the water-soluble resin is comprised of carboxymethylcellulose (CMC-H), carboxyethylcellulose (CEC-H), or the respective aluminum salt, barium salt, zinc salt, tin salt or manganese salt thereof.

4. A urine disposal means comprising the water setting paper of claim 1 inserted into a urine bottle.

5. A urine disposal means comprising the water setting paper of claim 1 inserted into a portable toilet.

6. The water setting paper of claim 1 comprising a sandwich of the high water-absorbency resin between two paper sheets each of which are comprised of pulp fibers, water-soluble resin, and high water-absorbency resin.

7. The water setting paper of claim 1 wherein
the higher water-absorbency resin is comprised of a synthetic resin produced by the crosslinking of polyacrylic acid, polystyrene sulfonic acid, polyvinyl pyridine, maleic anhydride, carboxylmethylcellulose, polyethylene oxide, polyvinyl alcohol or cellulose ether; and
the water-soluble resin is comprised of carboxymethylcellulose (CMC-H), carboxyethylcellulose (CEC-H), or the respective aluminum salt, barium salt, zinc salt, tin salt or manganese salt thereof.

8. The water setting paper of claim 1 wherein said sheet has three layers forming a sandwich structure having two outer layers and an inner layer; said inner layer being formed of said high water-absorbency resin and said two outer layers being formed of a mixture of said pulp fiber and said water-soluble resin.

9. The water setting paper of claim 2 wherein said sheet has three layers forming a sandwich structure having two outer layers and an inner layer; said inner layer being formed of said high water-absorbency resin and said two outer layers being formed of a mixture of said pulp fiber and said water-soluble resin.

10. The water setting paper of claim 3 wherein said sheet has three layers forming a sandwich structure having two outer layers and an inner layer; said inner layer being formed of said high water-absorbency resin and said two outer layers being formed of a mixture of said pulp fiber and said water-soluble resin.

11. The water setting paper of claim 7 wherein said sheet has three layers forming a sandwich structure having two outer layers and an inner layer; said inner layer being formed of said high water-absorbency resin and said two outer layers being formed of a mixture of said pulp fiber and said water-soluble resin.

12. The water setting paper of claim 11 wherein said water soluble resin is carboxymethylcellulose.

* * * * *